Figure 1:
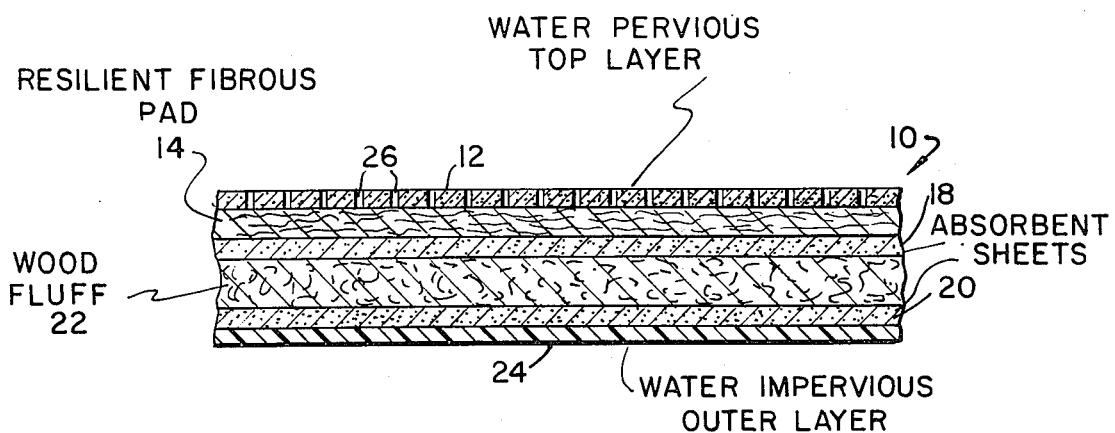

United States Patent [19]

Hernandez et al.

[11] 3,987,792

[45] Oct. 26, 1976

[54] DISPOSABLE DIAPER HAVING IMPROVED LIQUID RETENTION

[75] Inventors: John Michael Hernandez, East Brunswick; Karl H. Roberts, Flemington, both of N.J.

[73] Assignee: Colgate-Palmolive Company, New York, N.Y.

[22] Filed: July 31, 1975

[21] Appl. No.: 600,931

[52] U.S. Cl. .............................. 128/284; 128/287; 128/290 R
[51] Int. Cl.$^2$ ................. A41B 13/02; A61F 13/16
[58] Field of Search ............... 128/284, 287, 290 R, 128/296

[56] References Cited

UNITED STATES PATENTS

| | | | |
|---|---|---|---|
| 3,612,055 | 10/1971 | Mesek | 128/287 |
| 3,683,916 | 8/1972 | Mesek | 128/287 |
| 3,888,257 | 6/1975 | Cook | 128/296 |

*Primary Examiner*—Aldrich F. Medbery
*Attorney, Agent, or Firm*—Norman Blumenkopf; Murray M. Grill; Herbert S. Sylvester

[57] ABSTRACT

A disposable diaper comprising in order:

a water-pervious layer;

a spongy, resilient and compressible hydrophobic fibrous layer;

an absorbent core; and a water impervious layer, wherein said hydrophobic fibrous layer has a density of from about 0.01gm/cc to 0.03gm/cc and comprises non-woven, hydrophobic fibers having an average length of from about ¼ in. to 3½, said fibers being bonded together at at least a substantial number of their points of contact. The hydrophobic fibrous layer is pervious to fluids in the uncompressed condition; however, when compressed, as by the bodily weight of an infant clothed with the diaper, the layer becomes impervious to fluids, the compressed fibers intermeshing to form a seal or barrier.

11 Claims, 2 Drawing Figures

DISPOSABLE DIAPER HAVING IMPROVED LIQUID RETENTION

BACKGROUND OF THE INVENTION

1. Field Of The Invention

This invention relates generally to diapers and more particularly to disposable diapers having a barrier layer capable of effectively reducing migration of waste fluid from the absorbent core portion of a diaper to the water pervious layer adjacent the infant's skin.

2. Description Of The Prior Art

Disposable diapers comprising an absorbent core sandwiched between water-pervious and water-impervious outer layers are well known in the art. One of the more serious drawbacks of such disposable diapers as well as cloth diapers is their inability to effectively prevent "rewetting", i.e., recontacting of waste fluid contained in the absorbent core with the infant's skin. Thus, due to the weight and activity of the infant, a portion of the fluid is forcibly squeezed out of the absorbent core, the fluid readily penetrating the adjacent water-pervious layer and thus contacting the infant's skin. This results in considerable discomfort for the infant leading to diaper binding in the crotch area in particular, diaper rash, etc.

Attempts to mitigate the foregoing problems include the provision of diapers having a specific form of pleated construction to enhance absorptive capacity of the diaper. Thus, diapers of substantially rectangular configuration and having spaced-apart panels are usually of an undue width which allows the infant's legs to force the diaper downwardly so that it tends to sag away from the trunk of the body. This prevents proper utilization of the absorption capabilities of the diaper. Moreover, due to the spaced-apart position of the folded panels, and the consequent inefficient transfer of waste fluids to the absorbent core, wetting of the face sheet adjacent the skin of the infant is practically unavoidable.

OBJECT OF THE INVENTION

Thus, a primary object of the invention is to provide a diaper and particularly of the disposable type, wherein the foregoing disadvantages are eliminated or at least mitigated to a substantial extent.

Another object of the invention is to provide a disposable diaper capable of minimizing contact of waste fluid material in an absorbent core portion of the diaper with the infant's skin, to thus maintain the infant in a drier condition.

Yet another object of the invention is to provide a disposable diaper including an arrangement of parts for providing improved surface dryness and fit, and particularly in the crotch area of the diaper.

A still further object of the invention is to provide a disposable diaper having improved air circulation in the diaper cover area, the diaper providing an air cushion feel for the infant.

An additional object of the invention is to provide a disposable diaper having improved strength in the diaper pin or tab area, the physical form retention capacity of the diaper following urination by the infant being excellent due to the resilient or "spring back" character of the diaper assembly.

Yet an additional object of the invention is to provide a disposable diaper which effectively reduces the total number of diaper changes.

Other objects and advantages of the invention will become apparent as the description proceeds.

SUMMARY OF THE INVENTION

The foregoing objects are attained in accordance with the present invention which provides a disposable diaper comprising in order:

a water-pervious layer;

a spongy, resilient and compressible hydrophobic fibrous layer;

an absorbent core; and a water-impervious layer, wherein said hydrophobic fibrous layer has a density of from about 0.01gm/cc to 0.03 gm/cc and comprises non-woven, hydrophobic fibers having an average length of from about ¼ in to 3½ in, said fibers being bonded together at at least a substantial number of their points of contact, said hydrophobic fibrous layer in the uncompressed condition being pervious to fluids but when compressed, being substantially impervious to fluids, the compressed fibers intermeshing to form a fluid seal or barrier.

Figure 2:
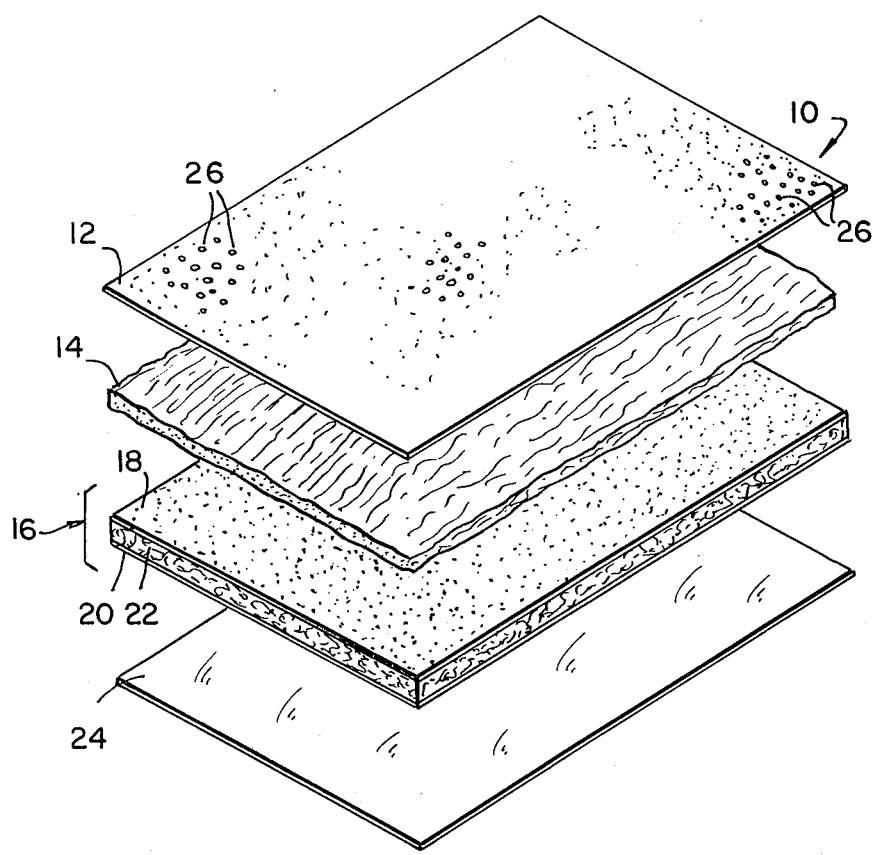

The invention will be explained having reference to the accompanying drawing wherein:

FIG. 1 is an exploded perspective view of a diaper constructed in accordance with the concepts of the invention; and, FIG. 2 is a vertical sectional view taken along the plane of line 2—2 in FIG. 1.

With continuing reference to the accompanying drawing, wherein like reference numerals designate similar parts throughout the various views, reference numeral 10 generally designates the diaper of the present invention. The diaper has four main component parts including water pervious layer 12, hydrophobic fibrous layer 14, an absorbent core generally indicated at 16 and comprising absorbent sheets 18 and 20 and absorbent layer 22 and water impervious layer 24.

Water pervious layer 12 is usually provided in the form of a non-absorbent, soft, non-woven tissue which may have a large number of small perforations 26. This layer is readily water pervious and facilitates passage of waste fluid toward the inner core portion 16 of the diaper. Water pervious layer 12 is adjacent the skin of the infant when the infant is diaper-clad and should therefore have a softness and non-irritating nature which ensures the comfort of the infant. Thus, water pervious layer 12 may be made of paper or of any of a wide variety of non-woven webs having the desired properties of softness to the touch, often termed "hand" or "feel", porosity and hydrophobic action with respect to fluid. Materials suitable for such use are in any event well known in the art.

Fibrous layer 14 can be prepared from hydrophobic, film-forming, resinous materials of various well known types. These include for example, resinous polyester comprising the reaction product of ethylene and dimethyl terephthalate, e.g., the resinous polyesters available under the trade name designations Dacron, Vycron, Kodel, Tereylene, etc.

Particularly preferred for use herein is the polyester fiber material commercially available from J. P. Stevens Nonwoven, Inc. under the trade name designation Bondaire. This material, which is a resinous polyester, comprises the reaction product of ethylene glycol and dimethyl terephthalate spray bonded with a heat resistant binder, such as the commercially available product known as "Firegard", to provide a resilient, fibrous pad structure.

The resin fibers used in preparing fibrous layer 14 should in general have an average length of from ¼ in. to 3½ in. In order to attain the desired properties regarding resiliency, sponginess and compressibility, layer 14 should have a density of from about 0.01gm/cc to 0.03gm/cc.

The resultant layer possesses a void volume i.e., a ratio of free space to fiber-occupied which tends to assure proper functioning of layer 14.

It is generally recommended that layer 14 have a thickness of from about 3/16 in to ½ in. Thus, if layer 14 is too thin, the desired fluid sealing action which obtains by virtue of fiber intermeshing upon compression of layer 14 may not occur. As a practical matter, excess thickness should be avoided since otherwise the diaper may be too bulky or untoward in handling not to mention possible discomfort to the infant.

Layer 14 as described can be prepared according to techniques well known in the art. Thus, fibers having the dimensions stated can be subjected to conditions of turbulence whereby to randomly orient the fibers such as by air blowing and/or tumbling and the like. The operation can be conducted at temperatures sufficiently high to soften the fibers resulting in a fusion of the fibers at at least a substantial number of their points of contact. Alternatively, the fibers may be treated with a bonding agent, such as by spraying, to provide the desired fibrous structure. Adhesive suitable for such use are well known in the art and include, for example, the commercial products Mycar 2671 (B. F. Goodrich) and E771 (Rohm and Haas).

The fibers comprising layer 14, due in large part to their hydrophobic character, are substantially form retaining while exhibiting effective flexibility, resiliency, compressibility i.e., spring-back characteristics, despite exposure to substantial quantities of fluid waste. The water-sealing characteristics of fibrous layer 14, as it applies to the prevention of rewetting in accordance with the present invention, can be explained as follows. With the diaper in place on the infant, water pervious layer 12 is adjacent the infant's skin. When the infant urinates, the urine passes through water pervious layer 12 and fibrous layer 14 into absorbent core 16 where it is absorbed by sheets 18 and 20 and layer 22. The weight of the infant tends to compress layer 14 causing the fibers to become intermeshed. This, in turn substantially reduces the void volume of layer 14 to the extent of forming a seal or barrier against re-entry of urine into water pervious layer 12.

The problem of urine re-entry is obviously particularly acute in those areas of the diaper cover subjected to the force of the infant's weight. However, in these specific areas, the barrier effect of layer 14 is most pronounced and effective. It is true that layer 14 where compressed can form a barrier to the flow of urine to the absorbent core. However, it is found in practice that the urine waste nevertheless readily passes into absorbent core 16 and particularly in those areas of the diaper immediately adjacent the compressed portion of layer 14.

Absorbent core 15 can comprise simply an envelope type construction including absorbent sheets or layers 18 and 20 filled with a fiber fluff 22 such as wood fluff, cotton fluff and the like. This envelope can be formed after blowing the absorbent fluff material as a coating onto either or both of absorbent sheets 18 and 20, the latter comprising absorbent paper such as tissues or the like. Alternatively, absorbent core 16 may comprise simply a plurality of plies of paper having a fluff coating thereon or plies of creped cellulose, wadding and the like.

Layer 24 is made of a suitable waterproof non-absorbent preferably resinous film-forming polymeric material which is liquid impervious for preventing liquid from passing entirely through the diaper. Sheet or layer 24 is preferably made of a polyethylene film. Other suitable materials include for example polypropylene and polyvinylchloride.

A latitude of modification, substitution and change is intended in the foregoing disclosure, and in some instances some features of the invention may be employed without a corresponding use of other features.

What is claimed is:

1. A disposable diaper comprising in order:
   a water-pervious layer;
   a spongy, resilient and compressible hydrophobic fibrous layer;
   an absorbent core, and
   a water impervious layer,
   wherein said hydrophobic fibrous layer has a density of from about 0.01gm/cc to 0.03gm/cc and comprises non-woven, hydrophobic fibers having an average length of from about ¼ in to 3½ in, said fibers being bonded together at at least a substantial number of their points of contact, said hydrophobic fibrous layer in the uncompressed condition being pervious to fluids but when compressed, being substantially impervious to fluids, the compressed fibers intermeshing to form a fluid seal or barrier.

2. A disposable diaper in accordance with claim 1 wherein said water pervious layer comprises non-absorbent, soft, non-woven tissue.

3. A disposable diaper in accordance with claim 2 wherein said water pervious layer is provided with a plurality of perforations.

4. A disposable diaper in accordance with claim 1 wherein said hydrophobic fibrous layer comprises resinous polyester fibers derived from the reaction product of ethylene glycol and dimethyl terephthalate.

5. A disposable diaper in accordance with claim 4 wherein said fibers are adhesively bonded together at at least a substantial number of their points of contact.

6. A disposable diaper in accordance with claim 1 wherein said hydrophobic fibrous layer has a thickness within the range of from about 3/16 in to ½ in.

7. A disposable diaper in accordance with claim 1 wherein said absorbent core comprises an absorbent fluff material sandwiched between opposed absorbent sheets.

8. A disposable diaper in accordance with claim 1 wherein said absorbent core comprises a plurality of plies of creped cellulose.

9. A disposable diaper in accordance with claim 1 wherein said water impervious layer comprises a resinous, filmforming polymeric material.

10. A disposable diaper in accordance with claim 9 wherein said impervious layer is selected from the group consisting of polyethylene, polypropylene and polyvinylchloride.

11. A disposable diaper comprising in order:
    a water pervious layer comprising a web of soft non-woven, non-absorbent material;
    a spongy, resilient and compressible hydrophobic fibrous layer;

an absorbent core comprising a fiber fluff material sandwiched between absorbent sheets, and a water-impervious layer comprising a film-forming, resinous, polymeric material wherein said hydrophobic fibrous layer has a density of from about 0.01gm/cc to 0.03gm/cc and comprises non-woven, hydrophobic fibers having an average length of from about ¼ in to 3½ in, said fibers being bonded together at at least a substantial number of their points of contact, said hydrophobic fibrous layer in the compressed condition being pervious to fluids but when compressed, being substantially impervious to fluids, the compressed fibers intermeshing to form a fluid seal or barrier.

* * * * *